Figure 1:
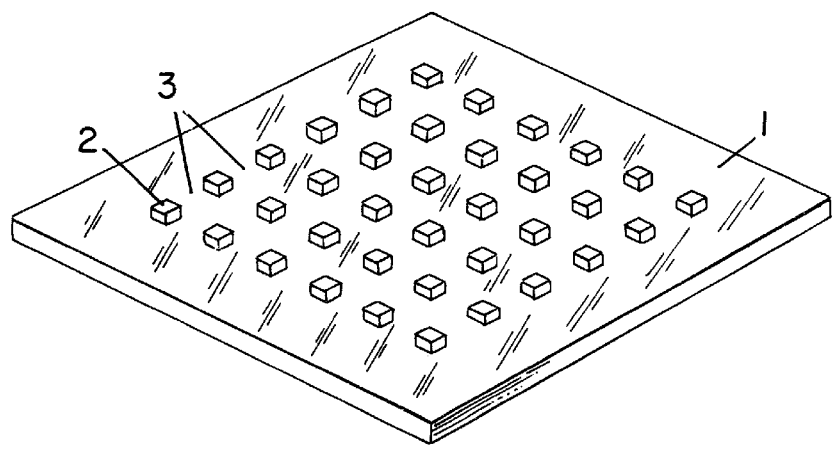

United States Patent [19]
Ershov et al.

[11] Patent Number: 5,770,721
[45] Date of Patent: Jun. 23, 1998

[54] METHOD OF MANUFACTURING A MATRIX FOR THE DETECTION OF MISMATCHES

[75] Inventors: Gennady Moiseevich Ershov; Andrei Darievich Mirzabekov, both of Moscow, Russian Federation

[73] Assignee: University of Chicago, Chicago, Ill.

[21] Appl. No.: 411,794

[22] PCT Filed: Aug. 5, 1994

[86] PCT No.: PCT/RU94/00180

§ 371 Date: May 19, 1995

§ 102(e) Date: May 19, 1995

[87] PCT Pub. No.: WO95/04834

PCT Pub. Date: Feb. 16, 1995

[30]     Foreign Application Priority Data

Aug. 11, 1993  [RU]  Russian Federation ............. 93040897

[51] Int. Cl.⁶ .......................... C07H 21/00; C07H 21/04; C12Q 1/68; G01N 21/00
[52] U.S. Cl. ............................. 536/25.3; 536/24.3; 435/6; 435/5; 435/91.1; 435/7.1; 435/7.72; 435/7.9; 435/91.2; 216/43; 216/48; 216/51; 216/41; 216/55; 216/65; 216/66; 216/75; 264/139; 264/176; 422/57; 422/61
[58] Field of Search ................................... 435/6, 5, 91.1, 435/7.1–7.9, 7.72; 430/320, 311, 313, 325; 536/25.3, 24.3; 436/525, 528, 809; 427/2.22; 429/44, 25; 156/628, 632.1, 638.1, 643.1; 205/139, 149, 153, 159, 162; 216/43, 48, 51, 41, 55, 65, 66, 75, 94; 264/139, 176; 422/57, 61

[56]       References Cited

U.S. PATENT DOCUMENTS 4,050,898  9/1977  Goffe et al. ........................ 23/253 TP 4,912,032  3/1990  Hoffman et al. ............................ 435/7
5,212,050  5/1993  Mier et al. ............................... 430/320

FOREIGN PATENT DOCUMENTS

| B1 0159719 | 10/1985 | European Pat. Off. . |
| B1 0322311 | 6/1989 | European Pat. Off. . |
| WO A1 89/10977 | 11/1989 | WIPO . |
| A1 0535242 | 10/1992 | WIPO . |
| WO A1 93/20233 | 10/1993 | WIPO . |
| WO A1 93/22462 | 11/1993 | WIPO . |

*Primary Examiner*—W. Gary Jones
*Assistant Examiner*—Dianne Rees
*Attorney, Agent, or Firm*—Foley & Lardner

[57]           ABSTRACT

This method for preparing micromatrices consists in applying a specially-patterned intermediate layer of laser-absorbing substance on a solid support. The configuration of the sublayer fully corresponds to the topology of the manufactured matrix. The intermediate layer is further covered by a continuous layer of gel, the gel and the material of the support being transparent towards laser radiation. The gel layer is irradiated by a laser beam for a time needed to evaporate simultaneously the gel in the places immediately above the laser-absorbing sublayer and the sublayer itself. Oligonucleotides from a chosen set are then attached to the formed gel 'cells', one oligonucleotide to each cell.

This method is intended for use in biotechnology, specifically for deciphering the nucleotide sequence of DNA.

4 Claims, 1 Drawing Sheet

METHOD OF MANUFACTURING A MATRIX FOR THE DETECTION OF MISMATCHES

FIELD OF THE INVENTION

The invention relates to molecular biology, and particularly to a method to prepare matrices for detecting mismatches.

BACKGROUND OF THE INVENTION

Known in the art is a method for preparing matrices containing a set of oligonucleotides of specified length: A, T, G, C, C, T, . . . etc. (PCT/GB 89/00460, 1989). Such matrices are useful in the detection of mismatches.

In the above method, oligonucleotides are synthesized directly on a glass support by successively masking certain regions of the glass surface with the strips of varied width made of silicon rubber.

For example, masking can be effected in the following way.

A first set of four bases, A, T, G, and C, is obtained by laying four wide strips on a rectangular glass plate (support).

A second set is produced by superimposing four identical strips in an orthogonal fashion, thereby getting a matrix consisting of 16 dinucleotides. Thereafter a third and a forth layer is put down, each consisting of four narrow strips (a fourth part of the width of the first strips).

In so doing, each layer of the narrow strips is put within one layer of wider strips. The final matrix contains a 256-membered set of tetranucleotides.

This process is repeated again and again, each time putting two perpendicular layers of narrow strips onto underlying two layers times of strips which are four time as large. Each layer adds one base to the oligonucleotide sequence and increases four-fold the number of unique sequences in the set.

The final size of the resulting matrix is determined by the width of said strips. For example, when strips as narrow as 1 mm wide are used, the matrix consisting of 256 oligonucleotides will occupy a space of about ~256 $mm^2$. With increasing number of oligonucleotides, the matrix becomes correspondingly large and will eventually become inconvenient to use. In particular it may be difficult to monitor simultaneously all cells, especially when fluorescent labeling is used.

The above method consists of many steps and is therefore time-consuming.

Another method for preparing matrices containing a set of oligonucleotides for detecting mismatches comprises providing a matrix containing a set of oligonucleotides of known length comprising the steps of coating a solid support gel layer; removing parts of said gel layer to conform it to the prescribed topology of the matrix so that the resulting gel spots are spaced from one another and their number is equal to the number of oligonucleotides in the set; and finally immobilizing presynthesized oligonucleotides from the set ATTGCC . . . to each gel spot, one by one (PCT/RU 92/00052, 1992). In that method, partial removal of gel to form "spacers" on the matrix is effected by mechanical scribing using a special stencil.

The above technology is less time-consumms since microdoses of presynthesized oligonucleotides are immobilized in the gel simultaneously, in one operation.

Moreover, for a given output signal the three-dimensional gel matrix will be smaller than the one that has been formed by synthesizing oligonucleotides directly in the near-surface layer of support.

However, mechanical scribing of the gel does not allow to obtain cells less than about 100 $\mu$m-per side, due to the mechanical damage caused to the gel edges (more or less rounded angles, possible peeling of gel from the solid support, etc.) which leads to deformation of the matrix topology and decreases the meaningful signal, down to total absence of the latter.

DISCLOSURE OF THE INVENTION

The present invention aims at developing a method to manufacture matrices for detection of mismatches, wherein shaping of the gel layer should be performed in accordance with the matrix topology in such a way as to ensure obtaining, at a high precision, the gel squares of a side from 10 to 50 $\mu$m safely attached to the support which, in turn, will allow one to miniaturize the matrix and simultaneously increase the number of its elements.

To realize the above goals, the known method to manufacture matrices dedicated to the detection of mismatches and containing a set of oligonucleotides of known length, wherein a continuous layer of gel is put down on a solid substrate, then certain parts of the gel are removed, and multiple discrete gel regions (depending on the number of oligonucleotides) are formed on the gel coat and spaced from one another in accordance with the prescribed topology of the matrix, followed by attachment of one of the oligonucleotides from the chosen set to a particular gel region, is improved in accordance with this invention in that before the gel coat is placed onto the substrate, the intended spacings on the matrices are covered with an intermediate layer which absorbs laser radiation while the gel and the support are virtually transparent towards the laser beam, and therefore said parts of the gel will be removed during exposure to the laser beam for a period of time which ensures that the gel will be evaporated in the places just above the intermediate layer as will the substance of the intermediate layer.

The preferred laser-radiation absorbing substance is aluminum.

The thickness of the intermediate sublayer is preferably proportional to the gel thickness, and is chosen so that it ensures evaporation of the gel at the spacings but excludes any thermal destruction of the substrate surface or the edges of the gel parts which should remain intact after the irradiation.

In accordance with this invention, said method of manufacturing matrices for detecting mismatches will allow one to produce with a high precision matrices with each side from approximately 10 to 30 $\mu$m.

It is also a fast method and it does not require the design of any unique equipment but can be implemented using commercially manufactured parts and instruments widely used in microelectronics.

A BRIEF DESCRIPTION OF THE DRAWINGS

Figure 2:
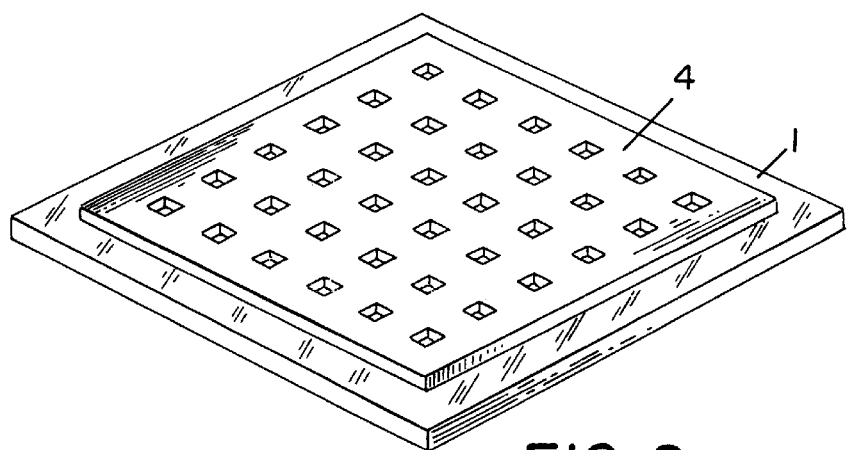
Figure 3:
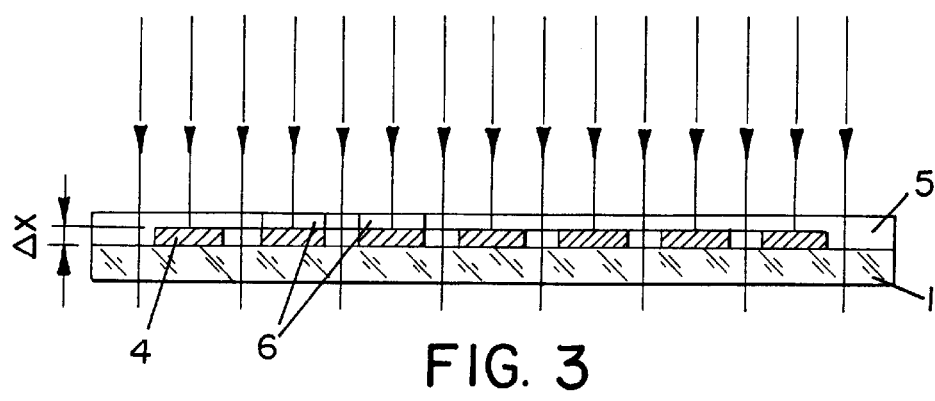

In the following, the invented method is further described through an example of its application and is illustrated by the drawings, among which FIG. 1 is an isometric presentation of a matrix for detecting oligonucleotides mismatches manufactured by said method;

FIG. 2 isometrically shows the above matrix at the moment when the intermediate sublayer has been put down in the process of manufacturing;

FIG. 3 shows the above matrix at the moment of its exposure to the laser beam (longitudinal cross-section).

BEST MODE OF CARRYING OUT THE INVENTION

The matrix in FIG. 1 comprises solid support 1 (in this example, a rectangular glass plate) and a multiplicity of regions 2 ("cells") on the surface thereof, which cells are distanced from one another by spacings 3. The surface of each cell 2, preferably of a square form is made of gel, preferably polyacrylamide gel. The cells are constituents of the matrix and they contain immobilized oligonucleotides of known length from the chosen set, each cell 2 bearing oligonucleotides of just one type.

The method to manufacture a matrix according to the invention (shown in FIG. 1) is as follows.

Following chemical pretreatment, the working surface of substrate 1 is covered by intermediate layer 4 (FIG. 2) consisting of a substance capable of absorbing laser radiation. As said substance, one can use metals, such as Ni or Al, Al being preferable.

Chemical pretreatment of substrate 1 prepares the working surface for forming better films of absorbing substance. For example, if the latter is of Al, then the surface of the glass substrate can be pretreated with a peroxide-ammonium solution and then rinsed off in a bath of deionized water.

Specially-shaped sublayer 4 can be formed by a two-step procedure, as follows:

The pretreated and washed surface 1 is covered by a continuous layer of aluminum;

Said Al film is photolitographed in accordance with the prescribed topology.

The first step can be performed, for example, by thermal evaporation under vacuum of Al by means of resistive evaporators. The preferred thickness of sublayer 4 is 0.1–0.3 $\mu$m.

The photolitographic procedures are well-described in the literature and can be applied unchanged.

On substrate 1 bearing the patterned sublayer 4 of laser-absorbing substance, a continuous layer of gel 5 is put down (FIG. 3). The gel 5 and the substrate 1 are both transparent towards the laser radiation. In this respect, polyacrylamide gels and agarose gels can be of choice, the preferred materials being polyacrylamide gels and glass substrates.

To provide better adhesion for the polyacrylamide gel so that covalent bonds can be formed between the glass and the gel, a layer of Bind-Silane is put down on the substrate for 30 min (Gammainetacryloxy-propyltrimetoxysilane), then it is removed with an appropriate solvent, washed with deionized water and dried up in a stream of gaseous nitrogen or in air.

Thin films of polyacrylamide gel are formed on the glass surface by pouring the gel solution into the capillary clearance between the substrate and a cover glass plate, whose substrate-facing surface has been made hydrophobic by special treatment.

The substrate and the cover glass plate, distanced by means of 20 $\mu$m-thick fluoroplastic spacers, are pressed together by clamps and the solution of polyacrylamide gel is drawn by the capillary forces into the clearance and after 5–10 minutes polymerized therein. The cover glass is then removed, and the substrate is washed by deionized water and dried. Thereafter the continuous gel layer 5 is irradiated by a laser beam (designated by the vertical arrows in FIG. 3) for a time which ensures both evaporation of the gel parts at places 6 located above the sublayer 4 of the absorbing substance and evaporation of the absorbing layer itself As a result of the irradiation, a multiplicity of gel spots 2 are formed on the substrate surface 1 (FIG. 1) spaced from one another by gaps 3 containing neither gel nor the substrate matter so that there remains only glass surface.

Any commercially-available laser with the working range of 0.53, 0.55, 0.63, 0.69, or 1.06 $\mu$m wavelength can be used as a laser beam source.

In said wavelength region, the absorption coefficients of polyacrylamide gels and glass do not exceed 1% whereas those of metal films, including Al, amount to dozens of percent absorption.

penetration of the radiation energy E(x) into material is described by the equation:

$$E(x) = E_0 \cdot (1-R) \cdot e^{-ax},$$

where $E_0$—incident energy;
R —coefficient of reflection;
a —coefficient of absorption.
The energy absorbed by the layer of the thickness $\Delta x$, $$\Delta E = E_0 \cdot (1-R) \cdot a e^{-ax} \Delta x$$

Thus the absorbed energy is maximal at the surface of the layer and it decreases monotonically with the depth. Most part of the energy is absorbed in the uppermost part of the layer of the thickness $1/a$. For metals, the a values are normally is $10^4 \div 10^5$ $cm^{-1}$, therefore said thickness is about $10^{-5}$–$10^{-6}$ cm.

The radiation energy that can be absorbed by intermediate sublayer 4 is proportional to its thickness $\Delta x$ and to the exposure time before evaporation.

At the same time, the above energy should be high enough to evaporate completely not only sublayer 4 but also those portions 5 of the gel that are located above sublayer 4. Deficient energy would lead to incomplete destruction of gel portions 5 that are to be removed, while excessive energy might damage the glass surface 1. An optimal irradiation energy to be delivered to gel regions 5 can be determined by varying either the radiation exposure or the thickness of sublayer 4.

However the maximal exposures are limited, on one hand, by the heat conductivity of gel and glass and, on the other hand, by a potential hazard to cause thermodestruction of gel portions 5 which must be saved.

In view of the above, optimal energies are chosen such that the thickness $\Delta x$ of intermediate layer 4 remains proportional to the thickness of gel 5.

Upon irradiation of gel layer 5, oligonucleotides are immobilized by known procedures into the resulting multiple gel spots 2 separated one from another by spacings.

For a better understanding of the present invention, this method is exemplified below for a matrix of 65,000 elements.

EXAMPLE

A glass slide, sized 45×45mn, thickness 1.5mm, was washed in two baths of ammonium-peroxide solution (containing 1 part of ammonia hydrate, 1 part of hydrogen peroxide and 6 parts of deionized water) for 15 min each at 70°–75° C.

Thereafter the glass support was washed in a three-cascade running bath of deionized water, and dried up in a stream of gaseous nitrogen. The entire surface of the glass support was covered under vacuum by a continuous aluminum layer of 0.2 mm thickness by using resistive evaporators.

A photoresistive film was then put down on the aluminum by centrifugation, dried and then exposed to UV irradiation through a mask to obtain a protective relief of photoresistive substance according to the image of the matrix to be produced. The unprotected areas of the Al film were removed by pickling in 50% ortophosphoric acid at 60°–70° C. The resulting Al sublayer on the glass support consisted of the perpendicular 60 $\mu$m-large lanes distanced by 30 $\mu$m from one another so that the obtained multiple 30×30 $\mu$m spots were arranged as a square grid.

Thereafter, the solid support was treated with Bind-Silane and covered with another glass slide that had been pretreated with Repel-Silane (LKB) and lubricated with Triton X-100. The two slides were distanced by a 20- $\mu$m spacer and the resulting clearance was filled with a mixture of 8% polyacrylamide, N,N'-methylenbisacrylamide (30:1), ammonia persulphate and TEMED and left for 1 hr to complete polymerization. After removal of the upper slide, the glass support coated by a 20-$\mu$m-thick polyacrylamide gel layer was treated with 50% hydrazine for 1 hr at room temperature.

Following the above pretreatment, the glass support having the outer gel coat with the underlying sublayer of Al strictly corresponding to the topology of the matrix to be manufactured was exposed to laser irradiation.

The irradiation treatment was performed under the following parameters:

radiation wavelength $\lambda$=1.06 $\mu$m;

maximal output power in the free generation regime=1 kJ;

pulse duration 3÷5 msec;

active element of glass with Nd$^+$(630×15 mm);

impulse frequency=0.03 Hz;

water cooling;

exposure time=$10^{-7}$ sec.

In the process of irradiation, the Al sublayer was evaporated completely. The heat liberated due to the evaporation of aluminum, caused evaporation of gel in the areas located above the intermediate sublayer. The gel coat located immediately on the glass remained intact and so did the glass surface below the evaporated aluminum.

Each cm$^2$ of the resulting matrix contained 12,000 gel squares (30×30 $\mu$m in size, 20 $\mu$m thick) distanced from one another by 60 $\mu$m spacings. The gel surface was intact and had sharp edges; no peeling was observed. The glass surface was also undamaged.

Thereupon, oligonucleotides were immobilized on the above gel matrix and the obtained micromatrix was used for detecting mismatches.

INDUSTRIAL APPLICABILITY

A method to prepare micromatrices for detecting mismatches can be used in medicine, molecular biology, and agriculture for the purposes of genetic diagnostics, DNA sequencing and mapping, and mutation detection.

We claim:

1. A method to prepare a patterned matrix for immobilizing oligonucleotides at distinct intervals on said matrix, comprising:

(a) precoating a solid support at distinct intervals with a sublayer of a substance to form a precoated matrix with a prescribed topology, wherein said solid support is virtually transparent to laser radiation and wherein said sublayer substance absorbs laser radiation;

(b) applying a continuous gel coat onto said precoated matrix wherein said continuous gel coat is also virtually transparent to laser radiation to form a gel coated matrix;

(c) irradiating said gel coated matrix with a laser beam so that upon irradiation those parts of the continuous gel coat which are immediately above said sublayer substance are evaporated together with said substance, wherein said evaporation forms a multiplicity of gel cells in the gel coated matrix which are spaced from one another by intervals forming a patterned matrix; and (d) immobilizing oligonucleotides from a chosen set of oligonucleotides into the gel cells wherein one oligonucleotide is immobilized per gel cell.

2. The method of claim 1 wherein said sublayer substance is aluminum.

3. The method of claim 1 wherein said sublayer substance has a thickness directly proportional to the thickness of the gel coat.

4. The method of claim 2 wherein said sublayer substance has a thickness directly proportional to the thickness of the gel coat.

* * * * *